United States Patent [19]

Gutman

[11] 4,119,716
[45] Oct. 10, 1978

[54] CERTAIN DIARYLDITHIOPHOSPHORODIAMIDATES AND THEIR USE AS BIOCIDES

[75] Inventor: Arnold D. Gutman, Berkeley, Calif.

[73] Assignee: Stauffer Chemical Company, Westport, Conn.

[21] Appl. No.: 819,653

[22] Filed: Jul. 27, 1977

[51] Int. Cl.² .......................... A01N 9/36; C07F 9/24
[52] U.S. Cl. .................... 424/220; 260/940; 260/954; 260/955; 260/959; 260/454; 424/210; 424/218
[58] Field of Search ............... 260/959, 954, 955, 940, 260/454; 424/220, 210, 218

[56] References Cited

U.S. PATENT DOCUMENTS

| 2,977,382 | 3/1961 | Millikan | 424/220 |
| 3,299,189 | 1/1967 | Millikan et al. | 260/962 |
| 3,516,965 | 6/1970 | Washbaun | 528/107 |
| 3,812,223 | 5/1974 | Tsuchiya | 26/987 |

Primary Examiner—Anton H. Sutto
Attorney, Agent, or Firm—Joel G. Ackerman

[57] ABSTRACT

New compounds having the formula

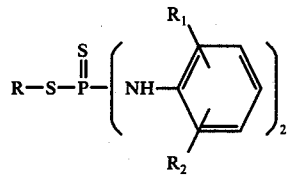

in which R is alkyl, phenyl, benzyl or p-chlorophenyl and $R_1$ and $R_2$ are hydrogen, halo, trifluoromethyl, lower alkyl, nitro, cyano or thiocyano. The compounds are useful as biocides, particularly as bactericides against *Staphylococcus aureus*.

152 Claims, No Drawings

CERTAIN DIARYLDITHIOPHOSPHORODIAMIDATES AND THEIR USE AS BIOCIDES

DESCRIPTION OF THE INVENTION

This invention relates to new diaryl substituted dithiophosphorodiamidates. More particularly, this invention relates to such compounds having the formula

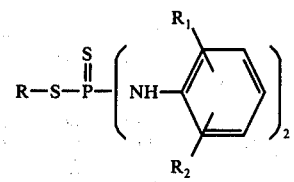

in which R is alkyl, phenyl, benzyl or p-chlorophenyl and $R_1$ and $R_2$ are halo, lower alkyl, trifluoromethyl, nitro, cyano, thiocyano or hydrogen, provided that at least one of $R_1$ and $R_2$ is other than hydrogen, and further provided that if $R_1$ or $R_2$ is cyano, R is methyl or p-chlorophenyl. $R_1$ and $R_2$ can be the same or different. As will be apparent from the data which follows, these compounds have been shown to have activity against bacteria - in particular, against the bacterium *Staphylococcus aureus*. Some of the compounds also show activity against certain fungi.

One embodiment of this invention comprises compounds having the formula in which the phenyl rings are mono-substituted, that is, $R_1$ is halo, lower alkyl, trifluoromethyl, nitro, cyano or thiocyano, and $R_2$ is hydrogen. A preferred embodiment of this group is one in which $R_1$ is halo, trifluoromethyl or thiocyano, especially in which $R_1$ is halo or trifluoromethyl.

Another embodiment of this invention comprises compounds having the above formula in which one of $R_1$ and $R_2$ is halo and the other is lower alkyl, trifluoromethyl, nitro, cyano or thiocyano. Preferred forms of this embodiment are those in which one of $R_1$ and $R_2$ is halo and the other is lower alkyl, trifluoromethyl or nitro.

Another embodiment of this invention comprises compounds having the above formula in which $R_1$ and $R_2$ are both trifluoromethyl.

Yet another embodiment of this invention comprises compounds having the above formula in which $R_1$ and $R_2$ are both halo. $R_1$ and $R_2$ may be the same or different halo groups.

In another respect, this invention comprises a process for combatting bacteria comprising applying to the bacteria, the locus thereof, or to a substance subject to bacterial attack, a bactericidally effective amount of a compound as defined herein.

In yet another aspect, this invention comprises a bactericidal composition of matter comprising a bactericidally effective amount of a compound as defined herein and an inert carrier or diluent.

In still another aspect, this invention comprises a composition of matter comprising a major proportion of a substance normally subject to bacterial attack or spoilage and a minor proportion of a compound as defined herein.

By the term "halo" is meant chloro, fluoro, bromo and iodo, preferably chloro, fluoro or bromo.

By the term "alkyl" is meant saturated acyclic hydrocarbyl groups, preferably containing from 1 to 10 carbon atoms such as methyl, ethyl, propyl, butyl, amyl, hexyl, heptyl, octyl, nonyl and decyl groups, including both straight chain and branched chain isomers. Straight chain (n-alkyl) groups are preferred.

By the term "lower alkyl" is meant such groups containing from 1 to 6, preferably from 1 to 4 carbon atoms, such as methyl, ethyl, n-butyl and the like.

In general, the compounds of the present invention can be prepared by reacting two equivalents of a substituted aniline with one equivalent of a dithiophosphorodichloride in the presence of two equivalents of a base or acid acceptor such as triethylamine, according to the reaction:

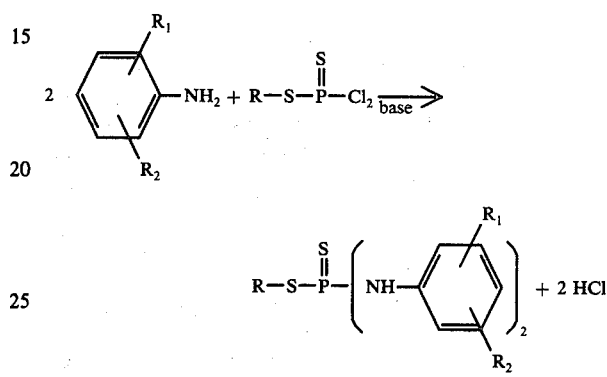

The reactants are heated under reflux in a suitable solvent such as toluene or acetonitrile and the desired product is obtained after washing with dilute acid and water, and removal of the solvent. The dithiophosphorodichloride can be made according to the procedure shown in U.S. Pat. No. 3,879,500 of Uhing et al.

The following are illustrative examples of preparation of compounds of the present invention.

EXAMPLE 1

Preparation of N,N'di(4-chlorophenyl)S-methyl dithiophosphorodiamidate (Compound 1 herein). 5.1 g. (0.04 mole) of 4-chloroaniline, 4.94 g. (0.04 mole) of triethylamine, 3.62 g. (0.02 mole) of S-methyl dithiophosphorodichloride and 200 ml. of toluene were combined in a 500 ml. round-bottom flask. The resulting mixture was heated under reflux, cooled, washed with 150 ml. HCl, and then with two 150 ml. portions of water. The toluene phase was dried with anhydrous $MgSO_4$ and removed under vacuum. Yield 5.0 g. (69% of theory) of the desired product, m.p. 165°–168° C.

EXAMPLE 2

Preparation of N,N'-di(3,5-dichlorophenyl)S-methyl dithiophosphorodiamidate (Compound 6 herein). In the same manner as in Example 1, using 3.24 g. (0.02 mole) of 3,5-dichloroaniline, 2.02 g. (0.02 mole) of triethylamine, 1.81 g. (0.01 mole) of S-methyl-dithiophosphorodichloride and 50 ml. of toluene. There was obtained 3.5 g. (81% of theory) of the desired product, m.p. 132°–133° C.

EXAMPLE 3

Preparation of N,N'-di[3,5-di-(trifluoromethyl)-phenyl]S-ethyldithiophosphorodiamidate (Compound 23 herein). In the same manner as in Example 1, using 6.87 g. (0.03 mole) 3,5-di(trifluoromethyl)-aniline, 3.03 g. (0.03 mole) triethylamine, 2.9 g. (0.015 mole) S-ethyl-dithiophosphorodichloride and 50 ml. of toluene, there was obtained 7.3 g. (84% of theory) of the desired product, $n_D^{30}$ 1.4725.

EXAMPLE 4

Preparation of N,N'-di-(4-chlorophenyl)S-(4-chlorophenyl) dithiophosphorodiamidate (Compound 25 herein). In the same manner as in Example 1, using 3.68 g. (0.028 mole) 4-chloroaniline, 2.9 g. (0.028 mole) triethylamine, 4.0 g. (0.014 mole) S-(4-chlorophenyl) dithiophosphorodichloride and 50 ml. of toluene, there was obtained 2.8 g. of the desired product, m.p. 203°–205° C.

EXAMPLE 5

Preparation of N,N'-di-(3-trifluoromethylphenyl)S-nbutyl dithiophosphorodiamidate (Compound 29 herein). In the same manner as in Example 1, using 5.8 g. (0.036 mole) 3-(trifluoromethyl)-aniline, 3.62 g. (0.036 mole) triethylamine, 4.0 g. (0.018) S-n-butyl dithiophosphorodichloride and 50 ml. of toluene, there was obtained 8.4 g. (99% of theory) of the desired product, $n_D^{30}$ 1.5183.

EXAMPLE 6

Preparation of N,N'-di-(4-chlorophenyl) S-n-butyl dithiophosphorodiamidate (Compound 30 herein). In the same manner as in Example 1, using 4.6 g. (0.036 mole) 4-chloroaniline, 3.6 g. (0.036 mole) triethylamine, 4.0 g. (0.018 mole) of S-n-butyl dithiophosphorodichloride and 50 ml. of toluene, there was obtained 5.4 g. (74% of theory) of the desired product, m.p. 140°–144° C.

The following Table 1 lists representative compounds of the invention prepared according to the above procedure.

Table 1

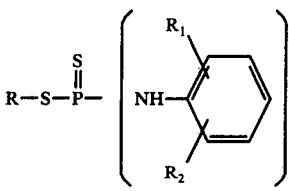

| Compound No. | R | $R_1$ | $R_2$ | $n_D^{30}$ or m.p. |
|---|---|---|---|---|
| 1 | CH₃ | 4-Cl | H | 165–168° C |
| 2 | CH₃ | 3-CH₃ | H | 99–101° C |
| 3 | CH₃ | 3-CF₃ | 4-Cl | 87–89° C |
| 4 | CH₃ | 4-Br | H | 175–178° C |
| 5 | CH₃ | 3-Cl | 4-Cl | 1.6140 |
| 6 | CH₃ | 3-Cl | 5-Cl | 132–133° C |
| 7 | CH₃ | 4-CN | H | * |
| 8 | CH₃ | 2-Cl | 5-CF₃ | 1.5281 |
| 9 | CH₃ | 2-CH₃ | 4-Br | * |
| 10 | CH₃ | 3-CF₃ | 5-CF₃ | ** |
| 11 | CH₃ | 3-CH₃ | 4-Cl | 1.6083 |
| 12 | CH₃ | 2-CH₃ | 4-Cl | 1.5925 |
| 13 | CH₃ | 3-CF₃ | 4-Cl | 1.5558 |
| 14 | CH₃ | 3-Cl | 4-F | 1.6063 |
| 15 | C₂H₅ | 3-CF₃ | 4-Cl | 1.5485 |
| 16 | C₂H₅ | 3-Cl | 4-Cl | * |
| 17 | C₂H₅ | 3-Cl | 5-Cl | 141–146° C |
| 18 | C₂H₅ | 2-Cl | 4-Cl | 1.6077 |
| 19 | C₂H₅ | 3-CF₃ | H | ** |
| 20 | C₂H₅ | 4-Br | H | 194–196° C |
| 21 | C₂H₅ | 4-Cl | H | 192–193° C |
| 22 | C₂H₅ | 3-Cl | 4-F | 1.5875 |
| 23 | C₂H₅ | 3-CF₃ | 5-CF₃ | 1.4725 |
| 24 | C₂H₅ | 2-Cl | 5-CF₃ | **** |
| 25 | Cl—⟨⟩— | 4-Cl | H | 203–205° C |

Table 1-continued

| Compound No. | R | $R_1$ | $R_2$ | $n_D^{30}$ or m.p. |
|---|---|---|---|---|
| 26 | Cl—⟨⟩— | 3-Cl | 5-Cl | *** |
| 27 | n-C₄H₉ | 3-Cl | 4-Cl | 1.6080 |
| 28 | n-C₄H₉ | 3-Cl | 5-Cl | 91–96° C |
| 29 | n-C₄H₉ | 3-CF₃ | H | 1.5183 |
| 30 | n-C₄H₉ | 4-Cl | H | 140–144° C |
| 31 | CH₃ | 2-F | H | 1.5833 |
| 32 | C₂H₅ | 2-F | H | 1.5730 |
| 33 | n-C₄H₉ | 2-F | H | ** |
| 34 | CH₃ | 3-F | H | ** |
| 35 | C₂H₅ | 3-F | H | ** |
| 36 | n-C₄H₉ | 3-F | H | 1.5705 |
| 37 | CH₃ | 4-F | H | 144–146° C |
| 38 | C₂H₅ | 4-F | H | 158–159° C |
| 39 | n-C₄H₉ | 4-F | H | 111–112° C |
| 40 | CH₃ | 3-CF₃ | 4-F | 1.5100 |
| 41 | C₂H₅ | 3-CF₃ | 4-F | 1.5145 |
| 42 | n-C₄H₉ | 3-CF₃ | 4-F | 1.5048 |
| 43 | CH₃ | 2-F | 4-F | 1.5572 |
| 44 | C₂H₅ | 2-F | 4-F | 1.5462 |
| 45 | n-C₄H₉ | 2-F | 4-F | 1.5030 |
| 46 | CH₃ | 3-Cl | 4-F | 1.5728 |
| 47 | C₂H₅ | 3-Cl | 4-F | 1.5775 |
| 48 | n-C₄H₉ | 3-Cl | 4-F | 1.5627 |
| 49 | CH₃ | 3-NO₂ | 4-F | 1.5860 |
| 50 | C₂H₅ | 3-NO₂ | 4-F | **** |
| 51 | n-C₄H₉ | 3-NO₂ | 4-F | 1.5838 |
| 52 | CH₃ | 2-CF₃ | 4-F | 1.5127 |
| 53 | C₂H₅ | 2-CF₃ | 4-F | 1.5042 |
| 54 | n-C₄H₉ | 2-CF₃ | 4-F | 1.4975 |
| 55 | C₆H₅ | 3-CF₃ | 5-CF₃ | 1.5025 |
| 56 | n-C₄H₉ | 3-CF₃ | 5-CF₃ | 1.4708 |
| 57 | n-C₄H₉ | 3-CF₃ | 4-Cl | 1.5442 |
| 58 | n-C₄H₉ | 2-Cl | 5-CF₃ | 1.5208 |
| 59 | n-C₈H₁₇ | 4-Cl | H | **** |
| 60 | ⟨⟩—CH₂— | 4-Cl | H | ** |
| 61 | n-C₈H₁₇ | 3-Cl | 5-Cl | ** |
| 62 | ⟨⟩—CH₂— | 3-Cl | 5-Cl | **. |
| 63 | n-C₈H₁₇ | 3-Cl | 4-Cl | 1.5757 |
| 64 | ⟨⟩—CH₂— | 3-Cl | 4-Cl | 1.6174 |
| 65 | n-C₈H₁₇ | 3-CF₃ | H | 1.5037 |
| 66 | ⟨⟩—CH₂ | 3-CF₃ | H | 1.5490 |
| 67 | n-C₈H₁₇ | 3-CF₃ | 5-CF₃ | 1.4614 |
| 68 | ⟨⟩—CH₂ | 3-CF₃ | 5-CF₃ | ** |
| 69 | n-C₈H₁₇ | 3-CF₃ | 4-Cl | 1.5225 |
| 70 | ⟨⟩—CH₂ | 3-CF₃ | 4-Cl | ** |
| 71 | i-C₃H₇ | 4-Cl | H | ** |
| 72 | i-C₃H₇ | 3-Cl | 5-Cl | ** |
| 73 | i-C₃H₇ | 3-Cl | 4-Cl | * |
| 74 | i-C₃H₇ | 3-CF₃ | H | 1.5265 |
| 75 | i-C₃H₇ | 3-CF₃ | 5-CF₃ | 1.4741 |
| 76 | i-C₃H₇ | 3-CF₃ | 4-Cl | * |
| 77 | Cl—⟨⟩— | 3-CF₃ | 5-CF₃ | 1.5143 |
| 78 | Cl—⟨⟩— | 3-CF₃ | 4-Cl | 1.5835 |
| 79 | Cl—⟨⟩— | 3-CF₃ | H | 1.5724 |
| 80 | n-C₃H₇ | 4-Cl | H | ** |
| 81 | i-C₄H₉ | 4-Cl | H | ** |
| 82 | n-C₃H₇ | 3-Cl | 5-Cl | ** |

Table 1-continued

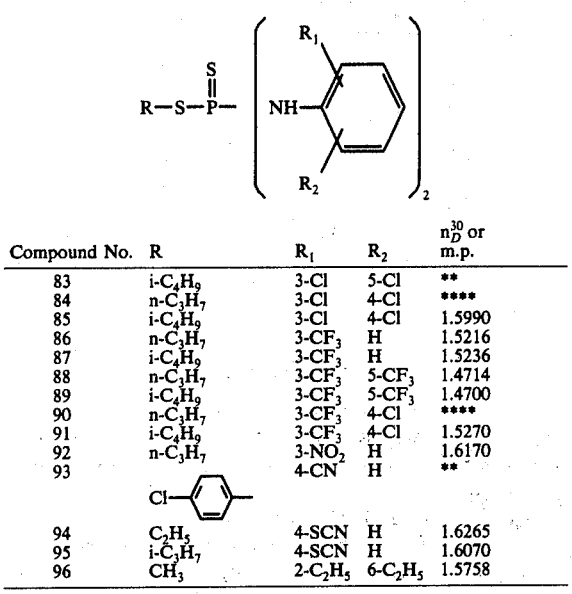

| Compound No. | R | $R_1$ | $R_2$ | $n_D^{30}$ or m.p. |
|---|---|---|---|---|
| 83 | i-$C_4H_9$ | 3-Cl | 5-Cl | ** |
| 84 | n-$C_3H_7$ | 3-Cl | 4-Cl | **** |
| 85 | i-$C_4H_9$ | 3-Cl | 4-Cl | 1.5990 |
| 86 | n-$C_3H_7$ | 3-$CF_3$ | H | 1.5216 |
| 87 | i-$C_4H_9$ | 3-$CF_3$ | H | 1.5236 |
| 88 | n-$C_3H_7$ | 3-$CF_3$ | 5-$CF_3$ | 1.4714 |
| 89 | i-$C_4H_9$ | 3-$CF_3$ | 5-$CF_3$ | 1.4700 |
| 90 | n-$C_3H_7$ | 3-$CF_3$ | 4-Cl | **** |
| 91 | i-$C_4H_9$ | 3-$CF_3$ | 4-Cl | 1.5270 |
| 92 | n-$C_3H_7$ | 3-$NO_2$ | H | 1.6170 |
| 93 | Cl–⟨⟩– | 4-CN | H | ** |
| 94 | $C_2H_5$ | 4-SCN | H | 1.6265 |
| 95 | i-$C_3H_7$ | 4-SCN | H | 1.6070 |
| 96 | $CH_3$ | 2-$C_2H_5$ | 6-$C_2H_5$ | 1.5758 |

*glass
**crude solid, melting point not taken
***low melting solid
****semi-solid

BACTERICIDAL EVALUATION

Tests of the compounds of this invention as bactericides were conducted in the following manner:

A. In Vitro Vial Tests

Tubes of sterilized nutrient and malt extract broth were prepared. Aliquots of the toxicant, dissolved in an appropriate solvent, were injected through the stopper, into the broth. The test organisms consisted of three bacteria, *Escherichia coli* (E.c.) Migula, *Staphylococcus aureus* (S.a.) Roseenbach and *Erwinia amylovora* (E.a.) (Burrill) Sinslow et al. The toxicants were tested at concentrations ranging from 50 ppm downward in the cases of Escherichia and Erwinia, and from 1000 ppm downward in the case of Staphylococcus. Three drops of the bacteria were injected into the nutrient broth. One week later the growth of each organism was observed and effectiveness of the chemical was recorded as the lowest concentration in ppm which provided 75% inhibition of growth as compared to untreated inoculated tubes. Some of the test compounds were observed to precipitate from the solution and thus obscure test results. To circumvent this problem, after the normal incubation period the cultures were streaked onto agar plates and the growth of the test organism, if any, was observed. Figures in parenthesis indicated partial control at the concentration specified and complete control at the next higher concentration tested.

The results of these tests are shown in the following Table 2.

Table 2

| Compound | E.c. | E.a. | S.a. |
|---|---|---|---|
| 1 | >50 | >50 | 0.25 |
| 2 | >50 | >50 | 0.1 |
| 3 | >50 | >50 | (0.025) |
| 4 | >50 | >50 | (0.25) |
| 5 | >50 | >50 | (0.05) |
| 6 | >50 | >50 | (0.025) |
| 7 | >50 | >50 | 5.0 |
| 8 | >50 | >50 | 1 |

Table 2-continued

| Compound | E.c. | E.a. | S.a. |
|---|---|---|---|
| 9 | >50 | >50 | (0.25) |
| 10 | >50 | >50 | 0.025 |
| 11 | >50 | >50 | 0.25 |
| 12 | >50 | >50 | (0.5) |
| 13 | >50 | >50 | 0.25 |
| 14 | >50 | >50 | (0.1) |
| 15 | >50 | >50 | 0.1 |
| 16 | >50 | >50 | 0.05 |
| 17 | >50 | >50 | 0.025 |
| 18 | >50 | >50 | 25 |
| 19 | >50 | >50 | 0.025 |
| 20 | >50 | >50 | 0.1 |
| 21 | >50 | >50 | 0.1 |
| 22 | >50 | >50 | 0.1 |
| 23 | >50 | >50 | 0.25 |
| 24 | >50 | >50 | 25.0 |
| 25 | >50 | >50 | (0.05) |
| 26 | >50 | >50 | (0.1) |
| 27 | >50 | >50 | (0.1) |
| 28 | >50 | >50 | (0.1) |
| 29 | >50 | >50 | (0.25) |
| 30 | >50 | >50 | (0.025) |
| 31 | >50 | >50 | 25 |
| 32 | >50 | >50 | 5 |
| 33 | >50 | >50 | 1000 |
| 34 | >50 | >50 | 5 |
| 35 | >50 | >50 | 1 |
| 36 | >50 | >50 | 0.25 |
| 37 | >50 | >50 | 5 |
| 38 | >50 | >50 | 1000 |
| 39 | >50 | >50 | 0.125 |
| 40 | >50 | >50 | 0.016 |
| 41 | >50 | >50 | 0.016 |
| 42 | >50 | >50 | 0.032 |
| 43 | >50 | >50 | 10 |
| 44 | >50 | >50 | 1 |
| 45 | >50 | >50 | 0.5 |
| 46 | >50 | >50 | 0.05 |
| 47 | >50 | >50 | (0.05) |
| 48 | >50 | >50 | 0.05 |
| 49 | >50 | >50 | 10.0 |
| 50 | >50 | >50 | 5.0 |
| 51 | >50 | >50 | (1.0) |
| 52 | >50 | >50 | 5.0 |
| 53 | >50 | >50 | (10.0) |
| 54 | >50 | >50 | 100 |
| 55 | >50 | >50 | 0.5 |
| 56 | >50 | >50 | (0.125) |
| 57 | >50 | >50 | 0.25 |
| 58 | >50 | >50 | 1000 |
| 59 | >50 | >50 | 25 |
| 60 | >50 | >50 | 0.063 |
| 61 | >50 | >50 | (0.5) |
| 62 | >50 | >50 | 0.0063 |
| 63 | >50 | >50 | (0.5) |
| 64 | >50 | >50 | (0.125) |
| 65 | >50 | >50 | (1) |
| 66 | >50 | >50 | 0.063 |
| 67 | >50 | >50 | (0.5) |
| 68 | >50 | >50 | (0.125) |
| 69 | >50 | >50 | 0.5 |
| 70 | >50 | >50 | 0.25 |
| 71 | >50 | >50 | 0.125 |
| 72 | >50 | >50 | 0.063 |
| 73 | >50 | >50 | 0.063 |
| 74 | >50 | >50 | 0.125 |
| 75 | >50 | >50 | 0.063 |
| 76 | >50 | >50 | 0.25 |
| 77 | >50 | >50 | 0.25 |
| 78 | >50 | >50 | 0.125 |
| 79 | >50 | >50 | 0.063 |
| 80 | >50 | >50 | 0.063 |
| 81 | >50 | >50 | 0.063 |
| 82 | >50 | >50 | 0.032 |
| 83 | >50 | >50 | 0.063 |
| 84 | >50 | >50 | (0.032) |
| 85 | >50 | >50 | 0.063 |
| 86 | >50 | >50 | (0.125) |
| 87 | >50 | >50 | 0.125 |
| 88 | >50 | >50 | 0.125 |
| 89 | >50 | >50 | 0.125 |
| 90 | >50 | >50 | 0.063 |
| 91 | >50 | >50 | 0.063 |
| 92 | >50 | >50 | (0.5) |
| 93 | >50 | >50 | 0.5 |
| 94 | >50 | >50 | 5 |
| 95 | >50 | >50 | 5 |
| 96 | >50 | >50 | 100 |

B. In Vitro Agar Screening Tests

This test measures the bactericidal properties of a compound when in contact with growing bacteria in an artificial medium. The test was conducted by adding 20 ml. portions of a suitable warm sterile agar solution into 20 × 100 mm. Petri dishes. Then, the test compound, in 0.5% acetone solution, was added to the Petri dishes at a level of 10 μg/ml. and mixed with the warm mobile agar solution. The treated agar solution was then allowed to come to room temperature and solidify. Cells of the chosen bacteria were streaked on the surface of the solidified agar and then incubated for such lengths of time that the untreated samples containing no toxicant showed luxurious growth typical of the particular bacteria. This time varied from 24 hours to 1 week depending on the bacteria employed. The bacteria were incubated at 37° C., and nutrient agar was used as the medium.

The extent of growth was noted at the end of the incubation period.

The bacteria used in these tests were selected from among: *Brevibacterium ammoniagenes* (B.a.), *Aerobacter aerogenes* (A.a.), *Escherichia coli* (E.c.), *Pseudomonas aeruginosa* (Ps.a.), *Staphylococcus aureus* (S.a.), *Streptococcus sp.* (mutans) (S.sp.), and *Bacillus cereus* (B.c.).

The results of tests of eleven of the compounds of the present invention at the 10 μg/ml. level are shown in Table 3.

Table 3

| Compound | B.a. | A.a. | E.c. | Ps.a. | S.a. | S.sp. | B.c. |
|---|---|---|---|---|---|---|---|
| 2 | C | — | — | — | C | C | |
| 3 | C | — | — | — | C | C | |
| 4 | C | — | — | — | P | C | |
| 5 | C | — | — | — | P | C | |
| 6 | C | — | — | — | P | | |
| 13 | P | — | — | — | — | | C |
| 23 | C | — | — | — | — | | C |
| 25 | — | — | — | — | — | | P |
| 26 | P | — | — | — | — | | C |
| 29 | C | — | — | — | — | | C |
| 30 | P | — | — | — | — | | C |

Key:
C - control
P - partial control
— - no control

C. Sulfate Reducing Bacteria In Vitro Test

This test measures the bactericidal properties of a compound when in contact with a sulfate reducing bacteria, specifically Desulfovibrio desulfuricans. The test was conducted by dissolving the test compound in acetone to give an 0.5% solution. The toxicants were added to vials containing sterile Sulfate API broth with tryptone under anaerobic conditions at levels to give a final toxicant concentration of 10 μg/ml. of solution. An inoculant solution of 0.5 ml. of the growing organism, *Desulfovibrio desulfuricans*, was added to the vials followed by sufficient sterile distilled water to give a total of 10 ml. of solution in the vials. The vials were incubated at room temperature for 3 to 5 days until untreated controls showed growth of the organism as indicated by the black color development in the vials. Table 4 shows the effect of a 10 μg/ml. concentration of five compounds of the present invention on this bacteria.

Table 4

| Compound No. | Effect |
|---|---|
| 2 | C |
| 3 | C |
| 4 | P |
| 5 | — |
| 6 | — |
| 13 | C |
| 23 | C |
| 25 | C |
| 26 | C |
| 29 | C |
| 30 | C |

Key:
C - Control
P - Partial control
— - no control

D. Dilution Tests

Tests were conducted on twelve compounds of the present invention according to the procedure described above under (A) at levels of 10 μg/ml. decreasing down to that at which the inhibitory effect of the compound substantially ceased. Table 5 shows minimum inhibitory concentrations for some compounds against *Staphylococcus aureus*. Figures in parentheses indicate partial control at the concentration specified and complete control at the next higher concentration tested.

Table 5

| Compound | Minimum Inhibitory Concentration μg/ml. |
|---|---|
| 1 | 1.56 |
| 2 | 3.12 |
| 3 | (0.78) |
| 4 | (1.56) |
| 5 | 1.56 |
| 6 | 0.78 |
| 13 | 0.196 |
| 23 | 0.78 |
| 25 | >10 |
| 26 | 0.39 |
| 29 | 1.56 |
| 30 | 0.78 |

Some comments concerning the bactericidal activity of these compounds are warranted by the results shown in Tables 2-5. First, it should be pointed out that the compounds possess bactericidal activity against a number of bacteria including sulfate reducing bacteria, although tests for activity against bacteria other than *Staphylococcus aureus* have not yet been completed on all compounds.

As to the activity of the compounds of this invention it appears that the nature of the R group is less relevant than the nature and/or position of substituents on the phenyl rings. For the most part, when R is lower alkyl, the activity of the compounds decreases as the number of carbon atoms increases. However, in general, the difference in activity is more marked when the position of substituents on the phenyl rings is varied. Substitution at either or both of the 2- and 4- positions on the ring seem to result in decreased activity as compared to substitution at the 3- and/or 5- position (meta-substitution). Thus, for instance, the 2-trifluoromethyl,4-fluorophenyl compounds 52, 53 and 54 were substantially less active against *Staphylococcus aureus* than the corresponding 3-, 4- substituted compounds 40-42. Similarly, the 3-fluoro-phenyl compounds 34-36 showed substantially greated activity than the 2-fluoro compounds 31-33. Compounds 34 and 36 showed approximately the same activity as the corresponding 4-fluoro compounds 37 and 39. However, the 3-fluorophenyl thioethyl compound 35 showed good activity while the corresponding 4-fluorophenyl compound 38 was surprisingly relatively ineffective.

The compounds of this invention may be applied in a number of situations in which bacterial control is desired. For example, they may be utilized to control slime resulting wholly or partly from bacterial action in aqueous systems such as lagoons, ponds, lakes, pools, cooling water systems and pulp and paper mill systems, as well as industrial process water which may operate as bacterial culture media, especially for sulfate reducing bacteria. In general, any process water which remains quiescent or under reduced rate of flow is subjected to growth of such bacteria. Typical process water systems include metallurgical operations employing wetting fluids, oil production (including subsurface disposal of water withdrawn from oil wells and water used to repressurize wells for secondary and tertiary oil recovery) and neutral drilling mud systems.

The compounds of this invention may also be used as a component of plasticized plastics, such as polyvinyl chloride, for prevention of discoloring or other undesirable effects of bacterial attack due to contact with moisture, for use in damp environments such as interior coatings for pipes and conduits, swimming pool liners, shower curtains and water-repellant fabrics and clothing made therefrom. These compounds may be incorporated into paints, glues, or other aqueous emulsion formulations to protect against bacterial attack during formulation and/or storage.

The compounds also may be used as components in soaps, detergents, fabric softeners, disinfectants, deodorants, and other deodorizing and/or odor-masking compositions, for industrial, institutional, laundry and other uses.

The compounds of this invention are generally embodied into a form suitable for convenient application and are generally utilized in concentrations of 0.1–10,000 ppm. For example, the compounds can be embodied into compositions which are provided in the form of emulsions, suspensions, solutions, dusts and aerosol sprays. In general, such compositions will contain, in addition to the active compound, the adjuvants which are found normally in such preparations. In these compositions, the active compounds of this invention can be employed as the sole bactericidal component or they can be used in admixture with other compounds having similar utility. The bactericidal compositions of this invention can contain, as adjuvants, organic solvents; water; emulsifying agents; surface active agents; talc; pyrophyllite, diatomite; gypsum; clays; propellants, such as dichlorodifluoromethane, etc. In connection with the activity of the presently disclosed compounds, it should be fully understood that it is not necessary that they be active as such. The purposes of this invention will be fully served if the compound is rendered active by external influences, such as light, or by some physiological action which occurs when the compound is ingested into the organism. When used in plastics, the compounds may be incorporated per se, for example by milling into the material prior to heating.

The precise manner in which the compositions of this invention are used in any particular instance will be readily apparent to a person skilled in the art.

What is claimed is:

1. A method for controlling bacteria comprising applying to the bacteria or the locus thereof a bactericidally effective amount of a compound having the formula

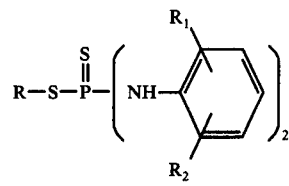

in which R is lower alkyl, phenyl, benzyl or p-chlorophenyl and $R_1$ and $R_2$ are halo, lower alkyl, trifluoromethyl, cyano, nitro, thicyano or hydrogen, provided that at least one of $R_1$ and $R_2$ is other than hydrogen, and further provided that if $R_1$ or $R_2$ is cyano, R is methyl or p-chlorophenyl.

2. A method according to claim 1 in which the bacterium to be controlled is selected from the group consisting of *Staphylococcus aureus, Brevibacterium ammoniagenes, Streptococcus sp.* (Mutans), *Bacillus cereus* and *Desulfovibrio desulfuricans.*

3. A method according to claim 2 in which the bacterium to be controlled is *Staphylococcus aureus.*

4. A method according to claim 1 in which $R_2$ is hydrogen.

5. A method according to claim 1 in which $R_1$ is halo, trifluoromethyl or thiocyano.

6. A method according to claim 5 in which $R_1$ is halo.

7. A method according to claim 6 in which $R_1$ is chloro.

8. A method according to claim 6 in which $R_1$ is bromo.

9. A method according to claim 6 in which $R_1$ is fluoro.

10. A method according to claim 9 in which $R_1$ is 3-fluoro.

11. A method according to claim 5 in which $R_1$ is trifluoromethyl.

12. A method according to claim 1 in which one of $R_1$ and $R_2$ is halo and the other is lower alkyl, trifluoromethyl, nitro, cyano, or thiocyano.

13. A method according to claim 12 in which one of $R_1$ and $R_2$ is halo and the other is lower alkyl, trifluoromethyl or nitro.

14. A method according to claim 13 in which one of $R_1$ and $R_2$ is halo and the other is lower alkyl.

15. A method according to claim 13 in which one of $R_1$ and $R_2$ is halo and the other is trifluoromethyl.

16. A method according to claim 1 in which $R_1$ and $R_2$ are both trifluoromethyl.

17. A method according to claim 1 in which $R_1$ and $R_2$ are both halo.

18. A method according to claim 17 in which $R_1$ and $R_2$ are both chloro.

19. A method according to claim 18 in which $R_1$ and $R_2$ are 3,4-dichloro.

20. A method according to claim 18 in which $R_1$ and $R_2$ are 3,5-dichloro.

21. A method according to claim 17 in which $R_1$ and $R_2$ are both fluoro.

22. A method according to claim 17 in which one of $R_1$ and $R_2$ is chloro and the other is fluoro.

23. A method according to claim 1 in which R is lower alkyl.

24. A method according to claim 1 in which R is phenyl.

25. A method according to claim 1 in which R is p-chlorophenyl.

26. A method according to claim 1 in which R is benzyl.

27. A bacterial composition of matter comprising:
(a) A bactericidally effective amount of a compound having the formula

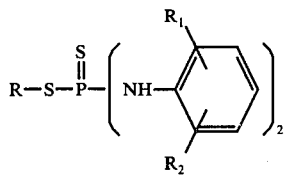

in which R is lower alkyl, phenyl, benzyl, or p-chlorophenyl and $R_1$ and $R_2$ are halo, lower alkyl, trifluoromethyl, cyano, nitro, thiocyano or hydrogen, provided that at least one of $R_1$ and $R_2$ is other than hydrogen and further provided that if $R_1$ or $R_2$ is cyano, R is methyl or phenyl; and
(b) an inert carrier or diluent.

28. A composition of matter comprising a major proportion of a substance normally subject to bacterial attack and a minor, bactericidally effective amount of a compound having the formula

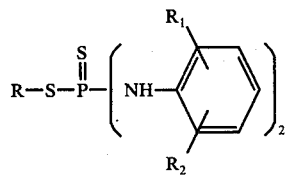

in which R is lower alkyl, phenyl, benzyl or p-chlorophenyl and $R_1$ and $R_2$ are halo, lower alkyl, trifluoromethyl, cyano, nitro, thiocyano or hydrogen, provided that at least one of $R_1$ and $R_2$ is other than hydrogen, and further provided that if $R_1$ and $R_2$ is cyano, R is methyl or phenyl.

29. A compound having the formula

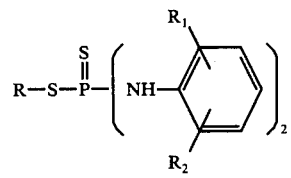

in which R is lower alkyl, phenyl, benzyl or p-chlorophenyl and $R_1$ and $R_2$ are halo, lower alkyl, trifluoromethyl, cyano, nitro, thiocyano or hydrogen, provided that at least one of $R_1$ and $R_2$ is other than hydrogen, and further provided that if $R_1$ or $R_2$ is cyano, R is methyl or p-chlorophenyl.

30. A compound according to claim 29 in which $R_2$ is hydrogen.

31. A compound according to claim 30 in which $R_1$ is halo, trifluoromethyl or thiocyano.

32. A compound according to claim 31 in which $R_1$ is halo.

33. A compound according to claim 32 in which $R_1$ is chloro.

34. A compound according to claim 32 in which $R_1$ is bromo.

35. A compound according to claim 32 in which $R_1$ is fluoro.

36. A compound according to claim 35 in which $R_1$ is 3-fluoro.

37. A compound according to claim 31 in which $R_1$ is trifluoromethyl.

38. A compound according to claim 29 in which one of $R_1$ and $R_2$ is halo and the other is lower alkyl, trifluoromethyl, nitro, cyano or thiocyano.

39. A compound according to claim 38 in which one of $R_1$ and $R_2$ is halo and the other is lower alkyl, trifluoromethyl or nitro.

40. A compound according to claim 39 in which one of $R_1$ and $R_2$ is halo and the other is lower alkyl.

41. A compound according to claim 39 in which one of $R_1$ and $R_2$ is halo and the other is trifluoromethyl.

42. A compound according to claim 29 in which $R_1$ and $R_2$ are both trifluoromethyl.

43. A compound according to claim 29 in which $R_1$ and $R_2$ are both halo.

44. A compound according to claim 29 in which $R_1$ and $R_2$ are both chloro.

45. A compound according to claim 44 to which $R_1$ and $R_2$ are 3,4-dichloro.

46. A compound according to claim 44 in which $R_1$ and $R_2$ are 3,5-dichloro.

47. A compound according to claim 43 in which $R_1$ and $R_2$ are both fluoro.

48. A compound according to claim 43 in which one of $R_1$ and $R_2$ is chloro and the other is fluoro.

49. A compound according to claim 29 in which R is lower alkyl.

50. A compound according to claim 49 in which R is methyl.

51. A compound according to claim 49 in which R is ethyl.

52. A compound according to claim 49 in which R is n-propyl.

53. A compound according to claim 49 in which R is isopropyl.

54. A compound according to claim 49 in which R is n-butyl.

55. A compound according to claim 49 in which R is isobutyl.

56. A compound according to claim 29 in which R is phenyl.

57. A compound according to claim 29 in which R is p-chlorophenyl.

58. A compound according to claim 29 in which R is benzyl.

59. A compound according to claim 29 in which R is methyl, $R_1$ is 4-chloro and $R_2$ is hydrogen.

60. A compound according to claim 29 in which R is methyl, $R_1$ is 3-trifluoromethyl and $R_2$ is hydrogen.

61. A compound according to claim 29 in which R is methyl, $R_1$ is 3-trifluoromethyl and $R_2$ is 4-chloro.

62. A compound according to claim 29 in which R is methyl, $R_1$ is 4-bromo and $R_2$ is hydrogen.

63. A compound according to claim 29 in which R is methyl, $R_1$ is 3-chloro and $R_2$ is 4-chloro.

64. A compound according to claim 29 in which R is methyl, $R_1$ is 3-chloro and $R_2$ is 5-chloro.

65. A compound according to claim 29 in which R is methyl, $R_1$ is 4-cyano, and $R_2$ is hydrogen.

66. A compound according to claim 29 in which R is methyl, $R_1$ is 2-chloro and $R_2$ is 5-trifluoromethyl.

67. A compound according to claim 29 in which R is methyl, $R_1$ is 2-methyl and $R_2$ is 4-bromo.

68. A compound according to claim 29 in which R is methyl, $R_1$ is 3-trifluoromethyl and $R_2$ is 5-trifluoromethyl.

69. A compound according to claim 29 in which R is methyl, $R_1$ is 3-methyl and $R_2$ is 4-chloro.

70. A compound according to claim 29 in which R is methyl, $R_1$ is 2-methyl and $R_2$ is 4-chloro.

71. A compound according to claim 29 in which R is phenyl, $R_1$ is 3-trifluoromethyl and $R_2$ is 4-chloro.

72. A compound according to claim 29 in which R is methyl, $R_1$ is 3-chloro and $R_2$ is 4-fluoro.

73. A compound according to claim 29 in which R is ethyl, $R_1$ is 3-trifluoromethyl and $R_2$ is 4-chloro.

74. A compound according to claim 29 in which R is ethyl, $R_1$ is 3-chloro and $R_2$ is 4-chloro.

75. A compound according to claim 29 in which R is ethyl, $R_1$ is 3-chloro and $R_2$ is 5-chloro.

76. A compound according to claim 29 in which R is ethyl, $R_1$ is 3-trifluoromethyl and $R_2$ is hydrogen.

77. A compound according to claim 29 in which R is ethyl, $R_1$ is 4-bromo and $R_2$ is hydrogen.

78. A compound according to claim 29 in which R is ethyl, $R_1$ is 4-chloro and $R_2$ is hydrogen.

79. A compound according to claim 29 in which R is ethyl, $R_1$ is 3-chloro and $R_2$ is 4-fluoro.

80. A compound according to claim 29 in which R is ethyl, $R_1$ is 3-trifluoromethyl and $R_2$ is 5-trifluoromethyl.

81. A compound according to claim 29 in which R is ethyl, $R_1$ is 2-chloro and $R_2$ is 5-trifluoromethyl.

82. A compound according to claim 29 in which R is p-chlorophenyl, $R_1$ is 4-chloro and $R_2$ is hydrogen.

83. A compound according to claim 29 in which R is p-chlorophenyl, $R_1$ is 3-chloro and $R_2$ is 5-chloro.

84. A compound according to claim 29 in which R is n-butyl, $R_1$ is 3-chloro and $R_2$ is 4-chloro.

85. A compound according to claim 29 in which R is n-butyl, $R_1$ is 3-chloro and $R_2$ is 5-chloro.

86. A compound according to claim 29 in which R is n-butyl, $R_1$ is 3-trifluoromethyl and $R_2$ is hydrogen.

87. A compound according to claim 29 in which R is n-butyl, $R_1$ is 4-chloro and $R_2$ is hydrogen.

88. A compound according to claim 29 in which R is methyl, $R_1$ is 2-fluoro and $R_2$ is hydrogen.

89. A compound according to claim 29 in which R is ethyl, $R_1$ is 2-fluoro and $R_2$ is hydrogen.

90. A compound according to claim 29 in which R is methyl, $R_1$ is 3-fluoro and $R_2$ is hydrogen.

91. A compound according to claim 29 in which R is ethyl, $R_1$ is 3-fluoro and $R_2$ is hydrogen.

92. A compound according to claim 29 in which R is n-butyl, $R_1$ is 3-fluoro and $R_2$ is hydrogen.

93. A compound according to claim 29 in which R is methyl, $R_1$ is 4-fluoro and $R_2$ is hydrogen.

94. A compound according to claim 29 in which R is n-butyl, $R_1$ is 4-fluoro and $R_2$ is hydrogen.

95. A compound according to claim 29 in which R is methyl, $R_1$ is 3-trifluoromethyl and $R_2$ is 4-fluoro.

96. A compound according to claim 29 in which R is ethyl, $R_1$ is 3-trifluoromethyl and $R_2$ is 4-fluoro.

97. A compound according to claim 29 in which R is n-butyl, $R_1$ is 3-trifluoromethyl and $R_2$ is 4-fluoro.

98. A compound according to claim 29 in which R is methyl, $R_1$ is 2-fluoro and $R_2$ is 4-fluoro.

99. A compound according to claim 29 in which R is ethyl, $R_1$ is 2-fluoro and $R_2$ is 4-fluoro.

100. A compound according to claim 29 in which R is n-butyl, $R_1$ is 2-fluoro and $R_2$ is 4-fluoro.

101. A compound according to claim 29 in which R is n-butyl, $R_1$ is 3-chloro and $R_2$ is 4-fluoro.

102. A compound according to claim 29 in which R is methyl, $R_1$ is 3-nitro and $R_2$ is 4-fluoro.

103. A compound according to claim 29 in which R is ethyl, $R_1$ is 3-nitro and $R_2$ is 4-fluoro.

104. A compound according to claim 29 in which R is n-butyl, $R_1$ is 3-nitro and $R_2$ is 4-fluoro.

105. A compound according to claim 29 in which R is methyl, $R_1$ is 2-trifluoromethyl and $R_2$ is 4-fluoro.

106. A compound according to claim 29 in which R is ethyl, $R_1$ is 2-trifluoromethyl and $R_2$ is 4-fluoro.

107. A compound according to claim 29 in which R is phenyl, $R_1$ is 3-trifluoromethyl and $R_2$ is 5-trifluoromethyl.

108. A compound according to claim 29 in which R is n-butyl, $R_1$ is 3-trifluoromethyl and $R_2$ is 5-trifluoromethyl.

109. A compound according to claim 29 in which R is n-butyl, $R_1$ is 3-trifluoromethyl and $R_2$ is 4-chloro.

110. A compound according to claim 29 in which R is n-butyl, $R_1$ is 2-chloro and $R_2$ is 5-trifluoromethyl.

111. A compound according to claim 29 in which R is n-octyl, $R_1$ is 4-chloro and $R_2$ is hydrogen.

112. A compound according to claim 29 in which R is p-chlorophenyl, $R_1$ is 4-chloro and $R_2$ is hydrogen.

113. A compound according to claim 29 in which R is n-octyl, $R_1$ is 3-chloro and $R_2$ is 5-chloro.

114. A compound according to claim 29 in which R is benzyl, $R_1$ is 3-chloro and $R_2$ is 5-chloro.

115. A compound according to claim 29 in which R is n-octyl, $R_1$ is 3-chloro and $R_2$ is 4-chloro.

116. A compound according to claim 29 in which R is benzyl, $R_1$ is 3-chloro and $R_2$ is 4-chloro.

117. A compound according to claim 29 in which R is n-octyl, $R_1$ is 3-trifluoromethyl and $R_2$ is hydrogen.

118. A compound according to claim 29 in which R is benzyl, $R_1$ is 3-trifluoromethyl and $R_2$ is hydrogen.

119. A compound according to claim 29 in which R is ethyl, $R_1$ is 2-chloro and $R_2$ is 4-chloro.

120. A compound according to claim 29 in which R is n-butyl, $R_1$ is 2-fluoro and $R_2$ is hydrogen.

121. A compound according to claim 29 in which R is ethyl, $R_1$ is 4-fluoro and $R_2$ is hydrogen.

122. A compound according to claim 29 in which R is n-butyl, $R_1$ is 2-trifluoromethyl and $R_2$ is 4-fluoro.

123. A compound according to claim 29 in which R is methyl, $R_1$ is 2-ethyl and $R_2$ is 6-ethyl.

124. A compound according to claim 29 in which R is n-octyl, $R_1$ is 3-trifluoromethyl and $R_2$ is 5-trifluoromethyl.

125. A compound according to claim 29 in which R is benzyl, $R_1$ is 3-trifluoromethyl and $R_2$ is 5-trifluoromethyl.

126. A compound according to claim 29 in which R is n-octyl, $R_1$ is 3-trifluoromethyl and $R_2$ is 4-chloro.

127. A compound according to claim 29 in which R is benzyl, $R_1$ is 3-trifluoromethyl and $R_2$ is 4-chloro.

128. A compound according to claim 29 in which R is isopropyl, $R_1$ is 4-chloro and $R_2$ is hydrogen.

129. A compound according to claim 29 in which R is isopropyl, $R_1$ is 3-chloro and $R_2$ is 5-chloro.

130. A compound according to claim 29 in which R is isopropyl, $R_1$ is 3-chloro and $R_2$ is 4-chloro.

131. A compound according to claim 29 in which R is isopropyl, $R_1$ is 3-trifluoromethyl and $R_2$ is hydrogen.

132. A compound according to claim 29 in which R is isopropyl, $R_1$ is 3-trifluoromethyl and $R_2$ is 5-trifluoromethyl.

133. A compound according to claim 29 in which R is isopropyl, $R_1$ is 3-trifluoromethyl and $R_2$ is 4-chloro.

134. A compound according to claim 29 in which R is p-chlorophenyl, $R_1$ is 3-trifluoromethyl and $R_2$ is 5-trifluoromethyl.

135. A compound according to claim 29 in which R is p-chlorophenyl, $R_1$ is 3-trifluoromethyl and $R_2$ is 4-chloro.

136. A compound according to claim 29 in which R is p-chlorophenyl, $R_1$ is 3-trifluoromethyl and $R_2$ is hydrogen.

137. A compound according to claim 29 in which R is n-propyl, $R_1$ is 4-chloro and $R_2$ is hydrogen.

138. A compound according to claim 29 in which R is isobutyl, $R_1$ is 4-chloro and $R_2$ is hydrogen.

139. A compound according to claim 29 in which R is n-propyl, $R_1$ is 3-chloro and $R_2$ is 5-chloro.

140. A compound according to claim 29 in which R is isobutyl, $R_1$ is 3-chloro and $R_2$ is 5-chloro.

141. A compound according to claim 29 in which R is n-propyl, $R_1$ is 3-chloro and $R_2$ is 4-chloro.

142. A compound according to claim 29 in which R is isobutyl, $R_1$ is 3-chloro and $R_2$ is 4-chloro.

143. A compound according to claim 29 in which R is n-propyl, $R_1$ is 3-trifluoromethyl and $R_2$ is hydrogen.

144. A compound according to claim 29 in which R is isobutyl, $R_1$ is 3-trifluoromethyl and $R_2$ is hydrogen.

145. A compound according to claim 29 in which R is n-propyl, $R_1$ is 3-trifluoromethyl and $R_2$ is hydrogen.

146. A compound according to claim 29 in which R is isobutyl, $R_1$ is 3-trifluoromethyl and $R_2$ is 5-trifluoromethyl.

147. A compound according to claim 29 in which R is n-propyl, $R_1$ is 3-trifluoromethyl and $R_2$ is 4-chloro.

148. A compound according to claim 29 in which R is isobutyl, $R_1$ is 3-trifluoromethyl and $R_2$ is 4-chloro.

149. A compound according to claim 29 in which R is ethyl, $R_1$ is thiocyano and $R_2$ is hydrogen.

150. A compound according to claim 29 in which R is isopropyl, $R_1$ is thiocyano and $R_2$ is hydrogen.

151. A compound according to claim 29 in which R is n-propyl, $R_1$ is 3-nitro and $R_2$ is hydrogen.

152. A compound according to claim 29 in which R is p-chlorophenyl, $R_1$ is cyano and $R_2$ is hydrogen.

* * * * *

UNITED STATES PATENT AND TRADEMARK OFFICE
CERTIFICATE OF CORRECTION

PATENT NO. : 4,119,716
DATED : October 10, 1978
INVENTOR(S) : Arnold D. Gutman

It is certified that error appears in the above–identified patent and that said Letters Patent are hereby corrected as shown below:

Claim 145 should read as follows:

A compound according to Claim 29 in which R is n-propyl, $R_1$ is 3-trifluoromethyl and $R_2$ is 5-trifluoromethyl.

Signed and Sealed this

Twenty-fifth Day of September 1979

[SEAL]

Attest:

LUTRELLE F. PARKER

Attesting Officer       Acting Commissioner of Patents and Trademarks